(12) United States Patent
Hoffmann

(10) Patent No.: US 7,977,509 B2
(45) Date of Patent: *Jul. 12, 2011

(54) PROCESS FOR THE PREPARATION OF ACID HALIDES

(75) Inventor: Ursula Hoffmann, Muttenz (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/418,902

(22) Filed: Apr. 6, 2009

(65) Prior Publication Data

US 2009/0192333 A1      Jul. 30, 2009

Related U.S. Application Data

(63) Continuation of application No. 12/105,339, filed on Apr. 18, 2008, now abandoned.

(30) Foreign Application Priority Data

Apr. 25, 2007   (EP) ..................................... 07106893

(51) Int. Cl.
*C07C 321/00*       (2006.01)
(52) U.S. Cl. ........................................................ 564/154
(58) Field of Classification Search .................. None
See application file for complete search history.

(56) References Cited

U.S. PATENT DOCUMENTS 2,899,458 A * 8/1959 Wilson et al. ................. 560/143
4,129,595 A   12/1978 Suzuki
7,435,849 B2 * 10/2008 Hoffmann et al. ............ 562/856

2003/0092708 A1   5/2003 Shinkai et al.
2007/0100154 A1   5/2007 Hoffmann
2008/0154059 A1   6/2008 Hoffmann et al.

FOREIGN PATENT DOCUMENTS

| JP | 1 020 439 | 7/2000 |
| WO | WO 98/54124 | 12/1998 |
| WO | WO 2004/056752 A1 | 7/2004 |
| WO | WO 2005/003116 | 1/2005 |

OTHER PUBLICATIONS

Shinkai et al, J Med Chem, 2000, 43, 3566-3572.*
Shinkai et al., J. Med. Chem., 43, pp. 3566-3572 (2000).
Hauser, Mal, Journal of the American Chemical Society, vol. 105, pp. 5688-5690 (1983), XP002416563.
March, J. *Advanced Organic Chemistry Thid Ed*. 1985) 388-389, XP002488845.
B.D. Roth, et al., J. Med. Chem., vol. 35, No. 9, pp. 1609-1617 (1992), XP002437815.
P.L. Creger, J. Am. Chem. Soc., vol. 92, No. 5, pp. 1397-1398 (1970), XP002437816.
Creger, P.L., Ann. Rep. Med. Chem., 12, pp. 278-287 (1977).
Petragnani et al., Synthesis, p. 521-578 (1982).

* cited by examiner

*Primary Examiner* — Sudhakar Katakam
(74) *Attorney, Agent, or Firm* — George W. Johnston; Dennis P. Tramaloni; Brian C. Remy

(57) ABSTRACT

A process for the preparation of acid halides of formula I

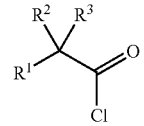

which are useful as intermediates in the preparation of i.a. pharmaceutically active compounds.

13 Claims, No Drawings

PROCESS FOR THE PREPARATION OF ACID HALIDES

PRIORITY TO RELATED APPLICATION(S)

This application is a continuation of application Ser. No. 12/105,339, filed Apr. 18, 2008, which claims the benefit of European Patent Application No. 07106893.6, filed Apr. 25, 2007. The entire contents of the above-identified applications are hereby incorporated by reference.

BACKGROUND OF THE INVENTION

The present invention is directed to a process for the preparation of acid halides which are useful as intermediates in the preparation of pharmaceutically active compounds, and in particular, for the preparation of compounds that inhibit cholesterylester transfer protein (CETP) such as those as described in EP 1,020,439. CETP is a plasma protein that facilitates the transport of cholesteryl esters and triglycerides between lipoproteins. It has been demonstrated that the inhibition of CETP increases the levels of high density lipoprotein (HDL).

U.S. Patent Application Publication No. 2007/0100154, discloses a "Process for the Preparation of Acid Chlorides" also useful as intermediates in the preparation of CETP inhibitors.

SUMMARY OF THE INVENTION

The present invention provides an improved production process for intermediates in the preparation of pharmaceutically active compounds and, in particular, for the preparation of intermediates used in the preparation of CETP inhibitors.

DETAILED DESCRIPTION OF THE INVENTION

In one aspect the present invention provides a process for the preparation of a compound of formula I

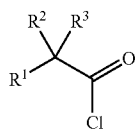

(I)

wherein:
$R^1$ is hydrogen, $C_1$-$C_8$alkyl or $C_2$-$C_8$alkenyl which are unsubstituted or substituted by one or more substituents selected from $C_1$-$C_8$alkoxy and $C_3$-$C_8$cycloalkyl; and
$R^2$ and $R^3$ are combined with the carbon atom to which they are attached to form $C_3$-$C_7$-cycloalkyl or $C_5$-$C_8$cycloalkenyl;
comprising reacting a compound of formula II

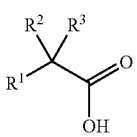

(II)

wherein $R^1$, $R^2$ and $R^3$ have the above meanings;

with thionylchloride in the presence of a tri-$C_1$-$C_5$alkylamine and an aliphatic hydrocarbon solvent.

The compounds of formula I may be used as intermediates in the synthesis of valuable pharmaceutical compounds, e.g. those as described in e.g. EP 1,020,439.

Accordingly, in another embodiment the present invention provides a process comprising the synthetic steps represented in the following scheme:

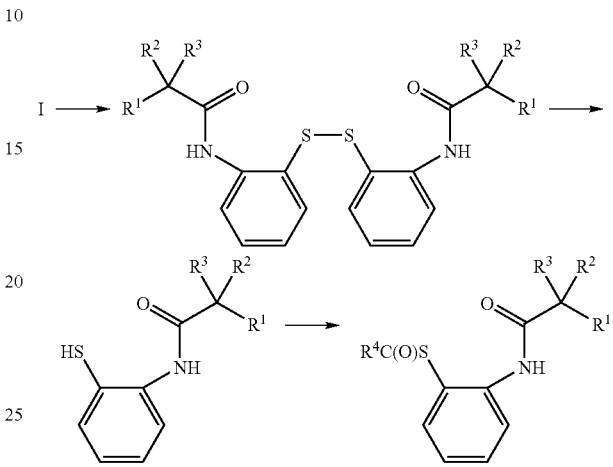

wherein $R^1$, $R^2$ and $R^3$ are as defined above and $R^4$ is $C_1$-$C_8$alkyl. In particular, the process comprises reacting a compound of formula I with bis(2-aminophenyl)disulfide to acylate the amino groups of the (2-aminophenyl)disulfide, reducing the amino-acylated disulfide product with a reducing agent such as triphenylphosphine, zinc or sodium borohydride to yield the thiol product, and acylating the thiol group in the thiol product with $R^4C(O)Cl$.

The additional steps may be performed, e.g., according to the procedures described in Shinkai et al., J. Med. Chem. 43:3566-3572 (2000).

Examples for $C_1$-$C_8$alkyl include methyl, ethyl, straight and branched propyl, butyl, pentyl, hexyl, e.g. $CH_2CH(CH_2CH_3)_2$, heptyl and octyl. For $R^1$, $C_1$-$C_8$alkyl is preferably $CH_2CH(CH_2CH_3)_2$. For $R^4$, $C_1$-$C_8$alkyl is preferably isopropyl.

Examples for $C_2$-$C_8$alkenyl include unsaturated carbon chains containing one or more double bonds at any possible position, e.g. vinyl, allyl, butenyl, pentenyl, hexenyl, heptenyl and octenyl.

Examples for $C_3$-$C_7$cycloalkyl include cyclopropyl, cyclobutyl, cyclopentyl, cyclohexyl and cycloheptyl. Preferred is e.g. cyclohexyl. Examples for $C_5$-$C_8$cycloalkenyl include cyclo-pentenyl, cyclohexenyl, cycloheptenyl, cyclooctenyl, cyclopentadienyl, cyclohexadienyl, cycloheptadienyl and cyclooctadienyl. Preferred are cyclopentenyl, cyclohexenyl and cycloheptenyl.

The term "tri-$C_1$-$C_5$alkylamine" denotes a compound of formula $R^4N(R^5)R^6$ wherein $R^4$, $R^5$ and $R^6$ independently are a $C_1$-$C_8$alkyl, and includes triethylamine, tributylamine, diethyl-methylamine, dimethyl-ethylamine and methylethyl-butylamine.

The term "aliphatic hydrocarbon" refers to a branched, straight or cyclic hydrocarbon chain, such as pentane, hexane, heptane, octane, cyclopentane, cyclohexane, or mixtures thereof. The most preferred aliphatic hydrocarbon is heptane.

The process may take place at a temperature in the range from 20 to 60° C., e.g. in a range from 40 to 55° C.

The acylating steps of the present invention are preferably conducted in the presence of a base. Preferred bases include organic bases with N-Methylmorpholine being a preferred organic base.

The amount of thionylchloride in relation to the compound of formula II, in the reaction mixture may be in the range from 1.0 to 2.0 equivalents of thionylchloride, e.g. from 1.0 to 1.2 equivalents, e.g. 1.2 equivalents.

The amount of the tri-$C_1$-$C_5$alkylamine in relation to the amount of the compound of formula II may be at a ratio of from 5 mol % to 0.1 mol %, e.g. from 0.3 mol % to 0.5 mol %, e.g. 0.3 mol %.

In another aspect the present invention provides a process for the preparation of a compound of formula I as above, comprising reacting a compound of formula II as above in the presence of a tri-$C_1$-$C_5$alkylamine and an aliphatic hydrocarbon solvent by continuously adding thionylchloride.

The term "continuously adding" denotes the addition of thionylchloride to a solution of compound II in an aliphatic hydrocarbon solvent, during a period of time from 10 minutes to 5 hours, depending on the batch size. The solution of compound II is heated to the desired temperature prior to the addition of thionylchloride. This method is different from the batch mode where all components are mixed at RT and the mixture is heated to the desired temperature.

In one embodiment the present invention provides a process for the preparation of a compound of formula I wherein $R^1$ is —$CH_2CH(CH_2CH_3)_2$. In another embodiment the present invention provides a process for the preparation of a compound of formula I wherein the tri-$C_1$-$C_5$alkylamine is triethylamine or tributylamine. In a preferred embodiment the present invention provides a process for the preparation of a compound of formula I wherein the tri-$C_1$-$C_5$alkylamine is tributylamine. When using tributylamine no precipitation of the hydrochloride salt of the tertiary amine occurs.

The compounds of formula II are commercially available or can be prepared by procedures known to the skilled person.

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom.

EXAMPLE

Preparation of 1-(2-Ethyl-butyl)-cyclohexanecarbonyl Chloride in the Presence of 0.003 Eq. Tributylamine and Heptane as the Solvent A mixture of 6.0 kg (28.3 mol) 1-(2-ethyl-butyl)-cyclohexanecarboxylic acid and 20.6 mL tributylamine (0.085 mmol) in 10 L heptane was warmed to 50° C. 2.5 L (34.5 mol) of thionyl chloride was added during 40 minutes at a temperature of 40-50° C. (reaction is endothermic, vigorous gas evolution) and the reaction mixture was kept at 53-55° C. An IPC-control after 60 minutes indicated complete conversion (0.04% 1-(2-ethyl-butyl)-cyclohexanecarboxylic acid and no 1-(2-ethyl-butyl)-cyclohexanecarboxylic acid anhydride). After removing volatile components under reduced pressure (70° C. bath, 13-8 mbar) 6.86 kg of the residue was obtained (assay 92.5% 1-(2-ethyl-butyl)-cyclohexanecarbonyl chloride, yield 97.2%)

The invention claimed is:

1. A process for the preparation of a compound of formula I:

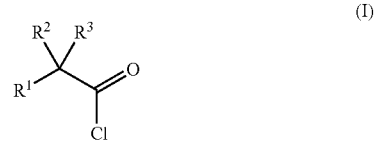

wherein:
$R^1$ is selected from the group consisting of:
(1) hydrogen,
(2) $C_1$-$C_8$alkyl, which is unsubstituted or substituted by one or more substituents selected from the group consisting of $C_1$-$C_8$alkoxy and $C_3$-$C_8$cycloalkyl, and
(3) $C_2$-$C_8$alkenyl which is unsubstituted or substituted by one or more substituents selected from the group consisting of $C_1$-$C_8$alkoxy and $C_3$-$C_8$cycloalkyl; and
$R^2$ and $R^3$ are combined with the carbon atom to which they are attached to form $C_3$-$C_7$cycloalkyl or $C_5$-$C_8$cycloalkenyl;
comprising reacting a compound of formula II:

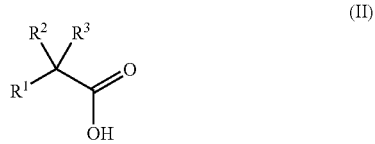

wherein $R^1$, $R^2$ and $R^3$ have the above meanings;
with thionylchloride in the presence of tributylamine and an aliphatic hydrocarbon solvent.

2. The process according to claim 1 additionally comprising the step of acylating a compound of the formula III:

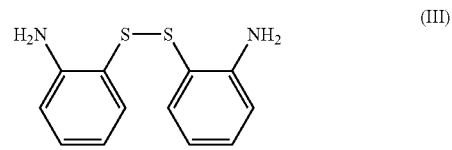

with a compound of formula I to yield a compound of formula IV:

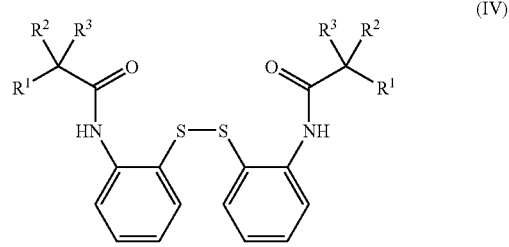

wherein $R^1$, $R^2$ and $R^3$ are as defined in claim 1.

3. The process according to claim 2 additionally comprising the step of reducing the compound of formula IV with a reducing agent to yield a compound of formula V:

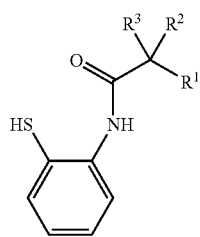

wherein $R^1$, $R^2$ and $R^3$ are as defined in claim 2.

4. The process according to claim 3 additionally comprising the step of acylating the compound of formula V with $R^4C(O)Cl$ to yield a compound of formula VI:

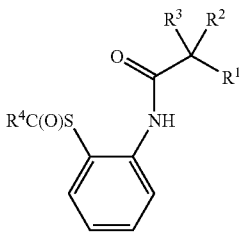

wherein $R^1$, $R^2$ and $R^3$ are as defined in claim 3 and $R^4$ is $C_1$-$C_8$alkyl.

5. The process according to claim 4 wherein $R^4$ is isopropyl.

6. The process according to claim 1 wherein the thionyl chloride is present in the range from 1.0 to 2.0 equivalents of thionylchloride in relation to the compound of formula II.

7. The process according to claim 1 wherein the amount of the tributylamine in relation to the amount of the compound of formula II is at a ratio of from 5 mol % to 0.1 mol %.

8. The process according to claim 1 wherein thionylchloride is continuously added.

9. The process according to claim 1 wherein in formula I $R^2$ and $R^3$ are combined with the carbon atom to which they are attached to form $C_3$-$C_7$cycloalkyl.

10. The process according to claim 1 wherein in formula I, $R^1$ is $CH_2CH(CH_2CH_3)_2$ and $R^2$ and $R^3$ are combined with the carbon atom to which they are attached to form cyclohexyl.

11. The process according to claim 2 wherein the acylating steps are performed in the presence of a base.

12. The process according to claim 11 wherein the base is an organic base.

13. The process according to claim 12 wherein the organic base is N-methylmorpholine.

\* \* \* \* \*